United States Patent
Fassi

(12) 
(10) Patent No.: US 6,271,258 B1
(45) Date of Patent: Aug. 7, 2001

(54) PROCESS FOR THE PREPARATION OF STABLE, NON-HYGROSCOPIC SALTS OF L(-)CARNITINE

(75) Inventor: Aldo Fassi, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 09/355,804

(22) PCT Filed: Feb. 24, 1998

(86) PCT No.: PCT/EP98/01039

§ 371 Date: Aug. 3, 1999

§ 102(e) Date: Aug. 3, 1999

(87) PCT Pub. No.: WO98/38157

PCT Pub. Date: Sep. 3, 1998

(30) Foreign Application Priority Data

Feb. 25, 1997 (IT) .............................................. MI97A0409

(51) Int. Cl.⁷ .................................................... A01N 37/12
(52) U.S. Cl. .......................... 514/561; 424/451; 514/529; 562/567
(58) Field of Search .............................. 424/451; 514/529, 514/561; 502/40.1, 402, 567

(56) References Cited

U.S. PATENT DOCUMENTS

| | | | | |
|---|---|---|---|---|
| 4,602,039 | * | 7/1986 | Cavazza | 514/561 |
| 4,933,490 | * | 6/1990 | Iannella | 562/401 |
| 5,073,376 | * | 12/1991 | Kohl et al. | 424/451 |
| 5,166,426 | * | 11/1992 | Jakob et al. | 562/567 |
| 5,591,450 | * | 1/1997 | Cavazza et al. | 424/451 |
| 5,651,997 | * | 7/1997 | Makino et al. | 424/682 |
| 5,747,536 | * | 5/1998 | Cavazza | 514/556 |

FOREIGN PATENT DOCUMENTS

| | | |
|---|---|---|
| 682 485 | 9/1993 | (CH) . |
| 0 150 688 | 8/1985 | (EP) . |
| WO 97 46512 | 12/1997 | (WO) . |

* cited by examiner

*Primary Examiner*—Gary Geist
*Assistant Examiner*—Taylor V Oh
(74) *Attorney, Agent, or Firm*—Nixon & Vanderhye

(57) ABSTRACT

An improved process for producing stable, non-hygroscopic salts of l(–)carnitine is disclosed, which comprises preparing at room temperature a pasty/semiliquid slurry of L(–) carnitine inner salt and water and adding to the slurry an organic dicarboxylic acid suitable for the formation of such salts

3 Claims, No Drawings

PROCESS FOR THE PREPARATION OF STABLE, NON-HYGROSCOPIC SALTS OF L(-)CARNITINE

This is a 35 U.S.C. §371 of PCT/EP98/01039 filed Feb. 24, 1998.

The present invention relates to an improved process for preparing stable, non-hygroscopic salts of L(-)carnitine.

These salts lend themselves to the preparation of solid pharmaceutical compositions suitable for oral administration, such as pills, tablets, chewable tablets, capsules, granulates, powders and the like, of which L(-)carnitine optionally formulated with the usual pharmacologically acceptable excipients, constitute the active ingredient.

These stable, non-hygroscopic salts also facilitate the production of solid compositions which may contain other active ingredients, e.g. with a nutritional and/or dietetic effect. These compositions which are administered orally constitute by far the most preferable administration form for a vast range of users and are increasingly establishing themselves on the so-called health food, medical food or neutraceutical market. These terms, which have yet to be rigourously defined from the regulatory point of view, denote foods or food components such as food supplements, dietetic products, energy foods, and the like, i.e. formulations which are not addressed to mainly or exclusively therapeutic purposes but which are aimed rather at enhancing well-being and at producing a general improvement in fitness and performance on the part of the consumer or at preventing metabolic disorders caused by dietary deficiencies or by the inadequate biosynthesis of essential endogenous substances as a result of advancing age.

The growing interest in L(-)carnitine in this field, too, stems from the increasingly widespread recognition, corroborated by scientific evidence, that L(-)carnitine in addition to its well-known therapeutic value in the treatment of various diseases, make a marked contribution towards supplying energy to the skeletal musculature and increasing the resistance to prolonged, intense stress in professional athletes or in any subject practising sport also at amateur level, enhancing the performance capability of such subjects.

In addition, L(-)carnitine constitutes an indispensable nutritional supplement for vegetarians, whose diets have a low carnitine content as well as a low content of the two amino acids, lysine and methionine, which are the precursors of the biosynthesis of L(-)carnitine in the kidneys and liver.

The same considerations apply not only to those subjects who have to live on a diet poor in protein for prolonged periods of time, but, in general, also to those subjects who, though not presenting any clearly definable pathological condition, feel debilitated, experiencing a particular state of stress or physical and/or mental fatigue.

All these applications indicate that the solid orally administrable compositions are the preferred presentation form, inasmuch as they make it particularly easy for users to take the substances and comply with optimal dosage regimens.

Of growing interest, moreover, is the use of L(-)carnitine in the veterinary field and as animal feed supplements in the breeding of livestock, some species of fish, and, most notably, valuable animals such as racehorses and thoroughbreds.

It has long since been known that L(-)carnitine is extremely hygroscopic and not very stable when it occurs as inner salt (or "betaine") as represented by the formula

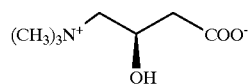

This leads to complex problems of processing, stability and storage both of the raw material and of the finished products. For example, L(-)carnitine tablets have to be packaged in blisters to keep them out of contact with the air, since, otherwise, even in the presence of normal humidity conditions, they would undergo alterations, swelling up and becoming pasty and sticky. In addition, owing to the inadequate stability, traces of trimethylamine are released which give the products an unpleasant fishy odour.

It is also known that the salts of L(-)carnitine present the same therapeutic, nutritional or dietetic activities, respectively, as the so-called inner salt (or "betaine") and can, therefore, be used in its place, provided these salts are "pharmacologically acceptable", i.e. they do not present unwanted toxic or side effects. In practice, then, the choice between the "inner salt" and a true L(-)carnitine salt will depend essentially on pharmacy considerations rather than on therapeutic, nutritional or dietetic considerations.

The pharmaceutical technologist is indeed interested in having at his disposal salts of L(-)carnitine which, unlike the inner salt, are solid and stable, particularly even in conditions of prolonged storage, which are non-hygroscopic and therefore can be easily processed and formulated with the usual excipients, using blending, tabletting devices, etc., of a traditional type, and which, in addition, pose no packaging problems when converted into finished products. These salts, both in the form of raw materials and when formulated in finished products, should not, even in non-ideal storage conditions, release traces of trimethylamine which would have a repulsive effect on the user.

There is now an extensive body of literature, particularly patents, disclosing the production of stable, non-hygroscopic salts of L(-)carnitine.

Japanese patent No. 303067 (Tanabe Seiyaku), published on 19.6.1962, publication No. 5199/19, discloses a process for the preparation of carnitine orotate, teaching that it is "advantageously less hygroscopic than carnitine and its typical salt, i.e. carnitine chloride, and can therefore be easily processed".

U.S. Pat. No. 4,602,039 (Sigma-Tau) granted on 22.7.1986 discloses acid maleate and acid fumarate of L(-)carnitine.

French patent application No. 82 11626 (Sanofi) published on 6.1.1984 publication No. 2 529 545, discloses L(-)carnitine acid sulphate and acid oxalate as non-hygroscopic salts.

Finally, EP 0434088 (LONZA) discloses the use of the non-hygroscopic L(-)carnitine L(+)tartrate (2:1) (the preparation and physico-chemical characterization of which were however described by D. Muller and E. Strack in Hoppe Seyler's Z. Physiol. Chem. 353, 618–622, April 1972) for the preparation of solid forms suitable for oral administration, such as tablets, capsules, powders or granulates.

The known processes described in the aforesaid patents entail the use of large volumes of water or hydroalcoholic mixtures or organic solvents (such as methanol, ethanol, isobutanol) wherein L(-)carnitine inner salt and/or the suitable acid [e.g. L(+) tartaric or fumaric acid] are dissolved for carrying out the salification and the subsequent crystallization. For instance, according to the previously cited EP 0434088, a boiling solution of L(+)tartaric acid in aqueous 90% ethanol is prepared and L(-)carnitine inner salt is then added thereto. This makes it necessary to concentrate large volumes of the carnitine salt-containing solution at high temperatures (50–60° C.) under reduced pressure (about 26664 Pa), with attendant noticeable energy waste. Moreover, the use of organic solvents entail high costs and serious problems of solvent recycling, environmental pollution and disposal of toxic waste materials.

The process of the present invention for preparing a stable, non-hygroscopic salt of L(−)-carnitine selected from the group consisting of L(−)carnitine L(+)tartrate (2:1) and L(−)carnitine acid fumarate (1:1) comprises:

(a) mixing at room temperature L(−)carnitine inner salt with the least amount of water necessary to obtain a slurry of pasty or semiliquid consistency;

(b) adding to the slurry at room temperature an equimolar amount of fumaric acid with respect to L(−)carnitine inner salt or one-half of the molar amount of L(−) tartaric acid and thoroughly blending the resulting reaction mixture;

(c) carrying out the solidification/dehydration of the reaction mixture by allowing the reaction mixture to stand in the open air at relative humidity not higher than 50% or accelerating the solidification/dehydration thereof by drying means; and (d) optionally grinding the solidified reaction mixture to provide the salt as a granulate or powder product.

In carrying out step (c), if it is preferred to accelerate the solidification/dehydration of the reaction mixture obtained in step (b), instead of allowing the reaction mixture to stand, a stream of air at a temperature slightly higher than room temperature and low relative humidity can be conveyed over the mixture or the mixture can be fed into a continuous drier or batch drier such as a turbotray drier, direct-heat rotary drier, drum drier, belt drier, spray drier, fluid bed drier and similar industrial driers well known to those skilled in chemical technology (see. e.g. "Drying" in Kirk-Othmer's Encyclopedia of Chemical Technology, vol. 8, pages 91–112, 1979).

Alternatively or in combination with the aforesaid operation, the solidification of the reaction mixture can be carried out by treating it with a very small volume of a non-toxic volatile, water-miscible solvent wherein the L(−) carnitine salt is insoluble, such as e.g. acetone.

The following non-limiting examples show the preparation of L(−)carnitine L(+)tartrate (2:1) and acid fumarate (1:1) according to the process of the present invention.

EXAMPLE 1

L(−)-carnitine L(+)-tartrate (2:1)

8.05 g (0.05 moles) of L(−)-carnitine and 1.5 mL of distilled water were mixed in a mortar giving a semiliquid slurry. 3.75 g (0.025 moles) of L(+)-tartaric acid were added to the slurry and the resulting mixture was thoroughly blended with a pestle, obtaining almost immediately a homogeneous, semitransparent, colourless "cream".

The solidification time of the tartrate was longer than that of the mucate, but the times became comparable to each other when an air stream at relative humidity of ten units lower than that used for mucate solidification was blown on the sample.

By treating the tartrate with an organic solvent, e.g. acetone, its final water content was lower than 1% by weight.

The L(−)-carnitine content, calculated on the anhydrous product, was 68.2%.

EXAMPLE 2

L(−)-carnitine fumarate (1:1)

8.05 g (0.05 moles) of L(−)-carnitine and 1.5 mL of distilled water were mixed in a mortar giving a semiliquid slurry. 5.80 g (0.05 moles) of fumaric acid were added to the slurry and the resulting mixture was thoroughly blended with a pestle, yielding almost immediately a homogeneous, semitransparent, colourless "cream" which solidified after some time. The product treated as in the previous example showed a final water content ≦1% by weight.

The L(−)-carnitine content, calculated on the anhydrous product, was 58.1% by weight.

It will be apparent that the moisture content of the end product depends on many factors such as the moisture content of the starting L(−)carnitine, the temperature and relative humidity of the air in the plant where the production operations are carried out, the overall processing duration and the particle size of the final product. Following exposure to relative humidity higher than 60%, in addition to crystallization water (if any), also imbibition water can be found.

It will also be apparent that the present process presents several, noticeable advantages over the prior art processes:

a) the process is carried out at room temperature and ambient pressure;

b) no organic solvents (or very small amounts thereof) are used, thus environmental pollution is avoided;

c) the yield is practically quantitative;

d) starting from anhydrous L(−)carnitine inner salt is not required: it is sufficient that its initial moisture content is known;

e) the consistency of the starting mixture can be varied, from a semisolid slurry to dense slurries of varying flowability, by simply regulating the added amount of water (10% to 30% by weight of the whole slurry). This allows a selection among the dehydration procedures to be made: from spontaneous water evaporation to procedures which entail the use of the aforesaid industrial driers; and f) in spontaneous evaporation, the dehydration time can be shortened by placing the product in an environment of low relative humidity (e.g. 30–40%) and/or by conveying on the product a stream of air of low relative humidity, at room temperature or slightly higher.

What is claimed is:

1. A process for preparing a stable, non-hygroscopic salt of L(−)carnitine selected from the group consisting of L(−) carnitine, L(+) tartrate (2:1) and L(−)carnitine acid fumarate (1:1), which process comprises the successive steps of:

(a) mixing at room temperature L(−)carnitine inner salt with the least amount of water necessary to obtain a paste or semiliquid slurry;

(b) adding to the slurry produced in step (a) at room temperature an equimolar amount of fumaric acid with respect to L(−)carnitine inner salt or one-half of the molar amount of L(+) tartaric acid and thoroughly blending the resulting reaction mixture;

(c) solidifying/dehydrating the reaction mixture of step (b) by allowing the reaction mixture to stand in the open air at relative humidity not higher than 50% or optionally accelerating the solidification/dehydration by drying; and (d) optionally grinding the solidified reaction mixture to provide the L(−)carnitine salt as a granulate or powder product.

2. The process of claim 1, wherein the drying is by a continuous drier, a batch drier, a turbotray drier, a direct-heat rotary drier, a drum drier, a belt drier, a spray drier or a fluid-bed drier.

3. The process of claim 1, wherein the amount of water used in step (a) necessary to obtain a pasty or semiliquid slurry is 10% to 30% by weight of the whole slurry.

* * * * *